United States Patent
Fuller et al.

(10) Patent No.: US 6,900,055 B1
(45) Date of Patent: May 31, 2005

(54) PREPARATION OF POROUS SILICONE RUBBER FOR GROWING CELLS OR LIVING TISSUE

(75) Inventors: Jess Paul Fuller, Leicestershire (GB); David Pegg, York (GB); Robert McLean Bird, Derby Shire (GB); Timothy Burgess Clifford, Leicestershire (GB); Tony Clayson, Leicestershire (GB)

(73) Assignee: Cellon S.A., Bereldange (LU)

( * ) Notice: Subject to any disclaimer, the term of this patent is extended or adjusted under 35 U.S.C. 154(b) by 0 days.

(21) Appl. No.: 09/830,592

(22) PCT Filed: Oct. 28, 1999

(86) PCT No.: PCT/GB99/03558

§ 371 (c)(1),
(2), (4) Date: Aug. 13, 2001

(87) PCT Pub. No.: WO00/24437

PCT Pub. Date: May 4, 2000

(30) Foreign Application Priority Data

May 28, 1998 (GB) ............................................. 9912641
Oct. 28, 1998 (GB) ............................................. 9823446

(51) Int. Cl.$^7$ ............................. A61F 2/00; C12N 5/06; C12N 5/08; C12N 11/08; C12N 11/04
(52) U.S. Cl. ...................... 435/395; 424/93.7; 424/423; 435/180; 435/182
(58) Field of Search ................................. 435/177, 180, 435/182, 395; 424/423, 93.7

(56) References Cited

U.S. PATENT DOCUMENTS

| 4,033,355 | A | | 7/1977 | Amundson |
| 4,377,077 | A | | 3/1983 | Granlund |
| 4,889,744 | A | | 12/1989 | Quaid |
| 4,937,194 | A | | 6/1990 | Pattillo et al. |
| 5,514,378 | A | * | 5/1996 | Mikos et al. ................ 424/425 |
| 5,614,095 | A | | 3/1997 | Degen et al. |
| 5,998,185 | A | * | 12/1999 | Fuller et al. ................. 435/180 |
| 6,130,080 | A | * | 10/2000 | Fuller ......................... 435/243 |
| 6,245,537 | B1 | * | 6/2001 | Williams et al. ............. 435/135 |
| 6,444,459 | B1 | * | 9/2002 | Fuller ......................... 435/243 |

FOREIGN PATENT DOCUMENTS

| EP | -0 277 009 A2 | | 8/1988 |
| EP | -0 326 278 A1 | | 8/1989 |
| EP | -0 450 671 A1 | | 10/1991 |
| WO | WO 94/16058 | * | 7/1994 |
| WO | WO 96/20050 | | 7/1996 |
| WO | WO-97/03744 A1 | | 2/1997 |
| WO | WO 97/08291 | * | 3/1997 |
| WO | WO-97/15242 A1 | | 5/1997 |
| WO | WO-97/21347 A1 | | 6/1997 |

* cited by examiner

*Primary Examiner*—David M. Naff
(74) *Attorney, Agent, or Firm*—Ropes & Gray, LLP

(57) ABSTRACT

A method of making a silicone rubber having a structure adapted for growth of cells or living tissue, which comprises contacting a silicone rubber precursor with a biologically-acceptable sacrificial filler, curing the resultant mixture and removing the sacrificial filler to form a structured silicone rubber. The sacrificial filler is preferably an inorganic salt that has been ground, and the salt is selected from metal halides, metal carbonates and metal bicarbonates.

39 Claims, 6 Drawing Sheets

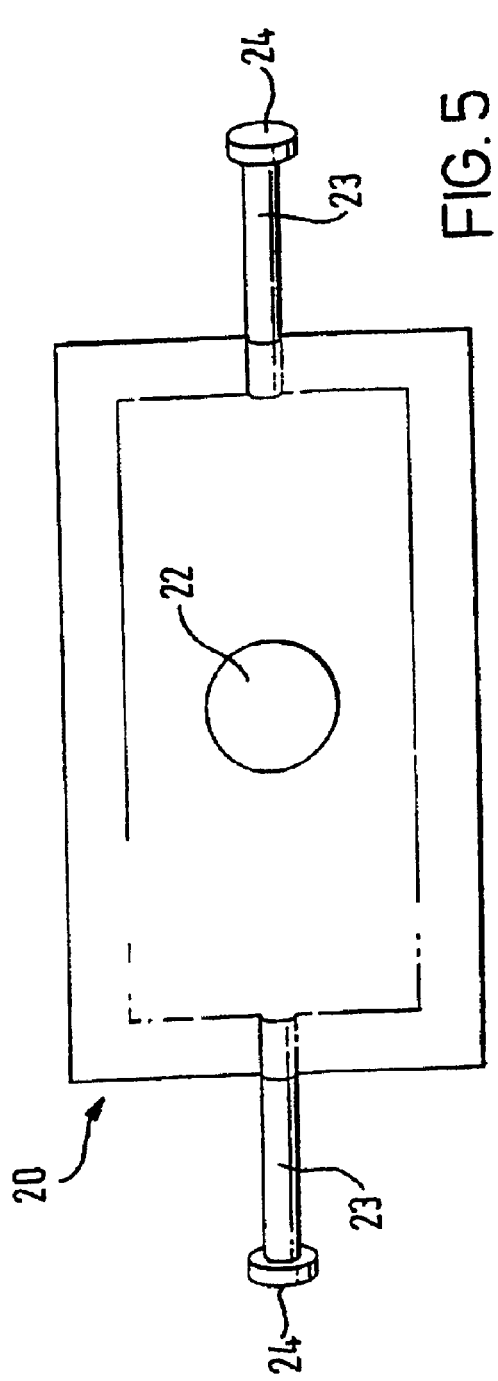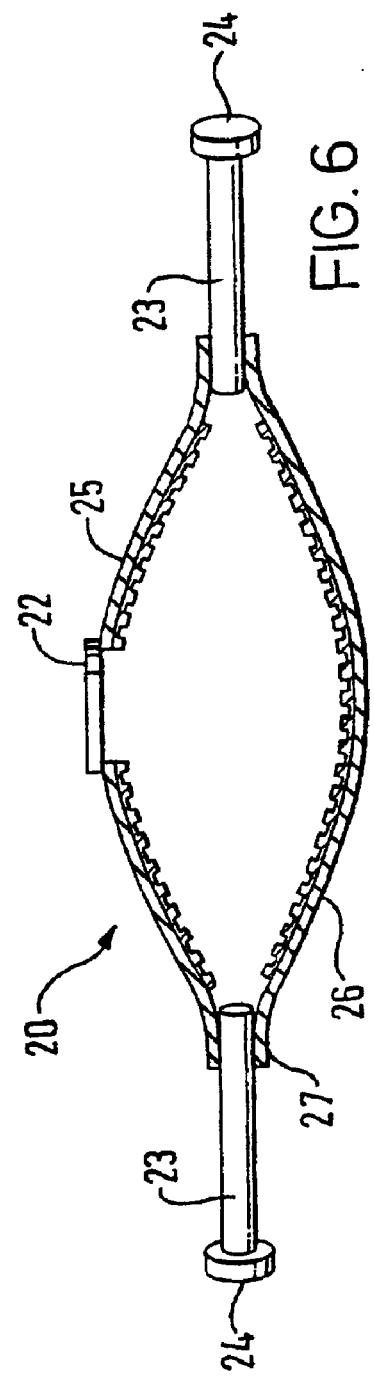

PREPARATION OF POROUS SILICONE RUBBER FOR GROWING CELLS OR LIVING TISSUE

BACKGROUND OF THE INVENTION

The present invention relates to methods for manufacturing silicone rubber that is adapted to promote cell adhesion and growth, and, in particular, to methods for providing silicone rubber with a modified surface or structure for enhanced cell attachment. The resultant silicone rubber is well-suited to a variety of tissue culture and medical applications.

Silicones surpass other elastomers in many performance categories because of their rigid silicon-oxygen chemical structure. The process of vulcanisation transforms this structure, allowing the silicon-oxygen polymer to become an elastic rubber. Silicone rubbers are stable throughout a temperature range of −46° C. to 232° C. They are odourless, tasteless and do not support bacterial growth. Silicone rubbers also do not stain or corrode with other materials. Most importantly, silicone rubbers are not physically or chemically degraded or altered by contact with body fluids, are not toxic or allergenic to human tissue and will not excite an inflammatory or foreign body reaction. Silicone rubbers can be formulated and tested for full bio-compatibility and compliance with guidelines for medical products. A further and particularly important advantage of silicone rubbers is that they have the highest oxygen permeability of known polymers.

Forming textured and porous silicone rubber allows all of these advantageous properties of silicone rubber to be exploited and enhanced. For example, a textured surface will not only greatly increase the available surface area for cell attachment, but will also encourage cell attachment. Furthermore, the increased surface area will increase the oxygen permeating through the silicone, enhancing the metabolic activity of the cells attached thereto. These advantages are very important in the various applications of textured and porous silicone rubbers discussed below.

SUMMARY OF THE INVENTION

In a first aspect of the invention, there is provided a method of making a silicone rubber having a structure adapted for growth of cells or living tissue, which comprises contacting a silicone rubber precursor with a biologically-acceptable sacrificial filler, curing the resultant mixture and removing the sacrificial filler to form a structured silicone rubber. Any suitable silicone rubber precursor may be used, depending upon the intended application of the resultant structured silicone rubber. Such silicone rubber precursors are widely available commercially, for example, from Dow Chemical Corporation, Midland, Mich., USA, or from GE Silicones Europe, Bergen op Zoom, the Netherlands. In a preferred embodiment, the silicone rubber precursor is one that can be cured or vulcanised at room temperature. This obviates the need to expose the mixture to elevated temperatures, which is particularly useful as some sacrificial fillers become unstable and decompose at elevated temperatures, thus making it difficult to control the final form of the structured silicone rubber. In a further embodiment, the biologically-acceptable sacrificial filler is biocompatible, such that it is innately non-toxic and does not leave a toxic residue. This is of particular importance where the structured silicone rubber is intended for use in tissue culture and medical applications, although a number of further factors also need to be considered when choosing a suitable sacrificial filler. For example, the sacrificial filler should preferably not react with the silicone rubber, either in its precursor form or in its cured state. The filler should also preferably be soluble in order to facilitate its removal by dissolution and the solvent used to dissolve the material should preferably not react with the silicone rubber. If the silicone rubber is to be cured at elevated temperatures, it is usually desirable to use a sacrificial filler that is stable at the curing temperatures, since materials that melt or decompose at high temperatures may be unsuitable, particularly if a structured silicone rubber having a high degree of regularity is desired. Finally, for commercial reasons, it is generally desirable that the sacrificial filler should be relatively inexpensive and readily available. In a preferred embodiment, the sacrificial filler is ground, prior to contacting the silicone rubber precursor. This has the advantage of allowing the resultant structure of the silicone rubber to be controlled much more accurately. Any suitable method for grinding the sacrificial filler may be used, although it has been found that wet-milling the sacrificial filler, prior to mixing with the silicone rubber precursor, gives good results. However, the sacrificial filler may also be ground by dry milling, preferably under an inert or dry atmosphere, such as under dry nitrogen or argon gas. In a preferred embodiment, the sacrificial filler is milled to a particle size of 0.01–10 $\mu$m, preferably 0.05–1 $\mu$m, and most preferably 0.1–0.4 $\mu$m. In a further embodiment, the sacrificial filler is granular and, preferably, crystalline, although certain amorphous fillers may also be suitable. Inorganic salts have been found to give particularly good results, although certain crystalline organic compounds, such as simple saccharides, may often be equally effective. Where the sacrificial filler is an inorganic salt, it is especially preferred to grind it first by milling it in an organic solvent, since this gives good control over resultant particle size. Preferably, the sacrificial filler is an inorganic salt selected from the group consisting of metal halides, metal carbonates and metal bicarbonates, especially one selected from the group consisting of lithium bicarbonate, sodium bicarbonate, potassium bicarbonate, lithium chloride, sodium chloride and potassium chloride. In an especially preferred embodiment, the sacrificial filler is sodium bicarbonate or sodium chloride, preferably of high purity, such as food grade sodium bicarbonate or sodium chloride. In this last embodiment, the sodium bicarbonate or sodium chloride is preferably wet-milled under xylene, although other volatile organic solvents may also be used. In a further embodiment, the ground sacrificial filler is classified, prior to contacting the silicone rubber precursor to ensure uniform particle size distribution, for example, by passing the ground material through sieves or by using a Malvern® Particle Sizer. In another embodiment, the sacrificial filler is removed by dissolution, preferably in an aqueous solvent. In the latter case, the sacrificial filler is desirably chosen so that it does not cause swelling of the silicone rubber when removed with an aqueous solvent. In a further embodiment, at least a portion of the free —OH groups that are normally present in the silicone rubber are chemically modified, so as to enhance or promote cell adherence. For example, free —OH groups may be chemically converted to form positively charged groups, for example, by reaction with diethylaminoethylbromide to give DEAE moieties, or to form negatively charged groups, for example, by reaction with iodoacetic acid, to give carboxylate moieties. In an alternative embodiment, the surface of the silicone rubber may be charged electrostatically, for example, by bombardment with electrons. Alternatively, the surface characteristics of the silicone rubber may be modified by applying a thin coating of a suitable polymer, so as to make it more adherent to certain cells, whilst still retaining a sufficient degree of gas permeability. Any suitable polymer may be used, such as one selected from the group consisting of polyolefins, polyvinyl resins, polyester resins, polyurethanes, polyamines, polyamides, polyethers and polysaccharides. In a preferred embodiment, the silicone rubber precursor also includes at least one additive that is not removed with the sacrificial filler and serves to impart desired physical properties on the resultant silicone rubber. For example, the additive may be a metal powder or carbon black, which can be used to render the silicone rubber electrically conductive. Alternatively, the additive may be stainless steel powder or iron oxide, which can be used to increase the density of the silicone rubber. The additive may also be an inert substance, such as glass, which can be used to render the silicone rubber mechanically rigid. However, many other suitable additives will also be apparent to those skilled in the art.

In a second aspect of the invention, there is provided a method of making a silicone rubber having a structure adapted for growth of cells or living tissue substantially in accordance with the invention in its first aspect, wherein a surface of the silicone rubber precursor is contacted with the sacrificial filler, so as to form a structured silicone rubber having a textured surface. The textured surface of the silicone rubber helps to facilitate attachment of adherent cells, as well as providing an increased surface area and, thus, number of sites for attachment of cells relative to an untextured surface. In an embodiment, the inventive method comprises forming a coating of a silicone rubber precursor on a substrate, contacting a surface of the coating with a biologically-acceptable sacrificial filler, curing the resultant mixture and removing the sacrificial filler to form a textured silicone rubber. Suitable silicone rubber precursors and biologically acceptable sacrificial fillers are essentially as described above in relation to the invention in its first aspect. In a preferred embodiment, the surface of the coating is contacted with the sacrificial filler under pressure, such that the sacrificial filler is substantially completely embedded in the coating. For example, the sacrificial filler may be dry-sprayed on to the surface of the coating, or may be applied loosely to the surface of the coating and then embedded by contacting the surface with a pressure roller. Preferably, the sacrificial filler is embedded to a depth of 0.1–1.0 mm, more preferably 0.1–0.5 mm, and more preferably 0.1–0.25 mm. In an alternative embodiment, the sacrificial filler is scattered or sprinkled over the surface of the coating, such that the sacrificial filler is only partially embedded in the surface. The latter technique can be used to provide the surface of the silicone rubber with a less uniform texture that is particularly suitable for growing certain types of adherent cells. Preferably, the resultant textured surface is micro-cupulated, i.e., cratered or pitted, the micro-cupules having a depth of less than 1 mm, preferably a depth of 0.5–0.1 mm. In a preferred embodiment, the micro-cupules measure less than 2 mm across, preferably less than 1 mm across, and, most preferably, less than 0.5 mm across. Silicone rubbers are available with a wide range of different physical properties, both in the uncured and cured state, and their methods of cure also differ widely. Consequently, the nature and properties of the silicone rubber used can affect the manufacturing process and the choice of a suitable silicone rubber precursor can be important. The silicone rubber precursor should be selected with due consideration to the manner in which the mixture is to be applied to the substrate, the conditions required for curing, and the desired properties of the end product. The uncured silicone rubber should usually have an appropriate viscosity for the method of its application to the substrate, and should retain its general form once the sacrificial filler has adhered to its surface. The conditions for curing must generally be compatible with both the substrate to which the uncured silicone rubber is applied and the sacrificial filler that adheres to the surface. Finally, the quality of the silicone rubber used should be selected in light of the intended application of the final product. In an especially preferred embodiment, silicone rubber paint RTV 118 (General Electric Co., Connecticut, USA) is used. In order to assist adhesion of the silicone rubber layer to certain materials, it may be necessary to apply a conventional adhesive, such as a mineral spirit-based primer, prior to deposition of the silicone layer. In a preferred embodiment, the primer used is silicone rubber primer SS 4155 (General Electric Co., Connecticut, USA). The micro-cupulated silicone rubber surfaces formed by the inventive method may be formed on or applied to any suitable substrates. When applied to cell culture vessels, such as culture flasks or roller bottles, the textured silicone rubber surfaces have been found to produce greatly increased yields in tissue culture processes. Such surfaces provide increased surface area for cell attachment, as well as promoting or encouraging cell attachment. The increased surface area also enhances oxygen supply to the surface. Thus, textured silicone layers according to the invention may be used in a variety of devices, particularly those where cell attachment is important.

In a third aspect of the invention, there is provided a method of making a silicone rubber having a structure adapted for growth of cells or living tissue substantially in accordance with the invention in its first aspect, wherein the sacrificial filler is dispersed throughout the silicone rubber precursor, and the structured silicone rubber is substantially porous. In this aspect, the inventive method creates a system of pores and channels throughout the silicone rubber structure. The pores of the silicone rubber provide sites of attachment for cells or tissues, so that the cells or tissues may be substantially trapped within the resultant structure. This system of pores can also act as a capillary system, increasing oxygen and nutrient supply to the surface of the structure. In a preferred embodiment, the method of making a porous silicone rubber comprises mixing the biologically-acceptable sacrificial filler with the silicone rubber precursor, curing the resultant mixture at a temperature below 180° C., and removing the sacrificial filler, to form a porous silicone rubber. Preferably, the silicone rubber is cured at a temperature between 100° C. and 175° C., more preferably between 120° C. and 170° C., more preferably between 140° C. and 160° C., and most preferably about 150° C. The silicone rubber precursors and the biologically acceptable sacrificial fillers that can be used are essentially the same as described above in relation to the invention in its first or second aspects. In another embodiment, the resultant mixture may be shaped prior to curing, preferably by moulding or extrusion. In a preferred embodiment, the average size of the pores formed is 1 μm–0.5 mm, preferably 10 μm to 0.2 mm, and more preferably 50 to 150 μm in diameter. Preferably, the porous silicone rubber is cut to a desired size or shape. For example, the porous silicone rubber may be cut in the form of small pellets that are capable of allowing cell growth within their pores but which can be readily separated from the culture medium by traditional separation methods, such as centrifugation or filtration. Silicone rubbers frequently contain innate fillers, such as fumed glass, which are added to produce desired viscosity, strength and other physical properties. The amount of sacrificial filler that can be mixed into the silicone rubber and, therefore, the extent of the porosity achieved is inversely proportional to the quantity of innate filler already present. Thus, a low viscosity silicone rubber containing small amounts of innate filler can accommodate a greater packing density of sacrificial filler than a high viscosity silicone rubber containing high levels of innate filler to give it a thicker consistency. The viscosity of the silicone rubber is also of importance when considering the manner in which the mixture is to be manipulated to give the end product. For example, if the mixture is to be extruded, a low viscosity silicone rubber, although able to hold a greater amount of sacrificial filler, may not be suitable, because separation of the filler can occur, particularly if extrusions of small cross-sections are required, as well as slumping of the mixture, due to its low viscosity, which can result in distorted shapes. However, if the mixture is to be spread into a sheet or moulded, then a low viscosity silicone rubber may well be appropriate because, for the same amount of filler, it is more easily manipulated. The green strength, i.e., the strength of the uncured silicone rubber precursor mixture, is also a factor for consideration. Low viscosity silicone rubber, when packed with sacrificial filler, for example, exhibits very poor green strength and is, thus, generally undesirable for extrusion. For extrusion applications, a very high viscosity silicone rubber would be ideal in principle, but, as so little sacrificial filler can be mixed into these materials, they are not usually a practical option. Therefore, a silicone rubber somewhere between the two must be chosen, such that sufficient innate filler can be included to maintain green strength but insufficient to be able to pack in sufficient sacrificial filler. The cure regime of the silicone rubber must also be taken into account. Where a rapid cure is required, for example, so as to maintain the geometry of an extrusion, heat cure systems are often required. However, these systems must be tailored such that the heat process does not have a deleterious effect on the filler. It may also be necessary to use room temperature curing systems if the material needs to be bound to an additional substrate that is unable to withstand elevated temperature, such as a thermoplastic, for example, The physical properties of the cured silicone rubber must also be considered. Where durability is an important issue, such as in the formation of tubes or sheets, then a silicone rubber having high tensile strength must be used. However, such silicone rubbers tend to be of higher viscosity and contain large amounts of innate filler and, hence, a compromise must be found. Where tensile strength is less of an issue, a low viscosity silicone rubber may be used, especially if there is no requirement for extrusion. Finally, the actual grade of silicone rubber is worthy of note. The final application of the material will determine the quality of the silicone rubber to be used. For medical and implantable applications, a high purity grade of material should be used, and, conversely, industrial grade silicone rubbers may be appropriate for applications, such as waste water treatment. In some instances, it may be desirable to include additives in the mixture in order to achieve certain characteristics, such as desired density, magnetic properties and the like. In the majority of cases, such additives would generally be in powder form and the considerations needed to choose suitable materials would be similar to those for the sacrificial filler. For example, if the silicone rubber is required to have an increased density, a high mass powder would be added in small quantities to make these adjustments and the choice of powder would follow criteria such as reactivity, toxicity and economics, etc. It has been found by the present invention that the use of certain sacrificial fillers can have an adverse effect on the resultant silicone rubber. For example, the use of sodium chloride can cause the silicone rubber to swell, depending upon the conditions. In order to avoid, this, it is desirable to use a sacrificial filler that does not cause swelling or adversely effect the resultant silicone rubber. Sodium bicarbonate has been found to be particularly effective in satisfying such criteria, although a number of other sacrificial fillers may be equally effective. If sodium bicarbonate is to be used as a sacrificial filler, it decomposes and, therefore, "blows" the material at temperatures above approximately 180° C. Consequently, it is necessary to adapt the manufacturing process so as to avoid temperatures above 180° C., for example, by selecting silicone rubbers, which cure at lower temperatures. Many of the alternative sacrificial fillers are toxic, leave toxic residues when dissolved, or are problematic at moderate temperatures required for working with silicone rubber. The silicone rubbers formed using the methods in accordance with the first, second and third aspects of the invention have properties that make them particularly well-suited for use in a range of biomedical devices and apparatus.

In a fourth aspect of the invention, there is provided a culture chamber for use in a method of culturing microbiological material, which comprises at least one gas-permeable wall or portion of a wall, and a textured interior growth surface arranged for contact with the microbiological material being cultured. The general principles of culturing cells in vitro are well-established in the field of biotechnology, with the term "cell culture" being usually understood to refer to both growth and maintenance of cells. In a preferred embodiment, the gas-permeable wall and the textured interior growth surface are each formed from an organic polymer, optionally the same organic polymer. The gas-permeable wall or potion of a wall of the culture chamber may also provide the textured interior growth surface, such that cells may grow directly on a textured growth surface on the gas-permeable membrane, thus allowing high cell densities. In a preferred embodiment, the gas-permeable wall or portion of a wall comprises a silicone rubber membrane. In an especially preferred embodiment, the textured interior growth surface is obtained or obtainable by a method according to the invention in its second aspect. Preferably, the culture chamber has at least one port extending between the interior and the exterior of the chamber. More often, however, there will be at least two ports, preferably including an inlet and an outlet port. An additional septum port may also be provided, to reduce the risk of contamination when introducing various substances to the culture chamber. In an embodiment, at least one or both of the inlet and outlet ports are septum ports. In an especially preferred embodiment, the culture chamber is in the form of a flexible bag or envelope. A variety of different apparatus is known for culture of cells in vitro. In recent years, flexible culture bags have become increasingly popular, offering a number of advantages over traditional cell culture apparatus, such as multi-well plates, flasks, roller bottles and spinner flasks. For example, culture bags represent closed systems, thus reducing the risk of contamination, as well as taking up less storage and incubator space. In addition such culture bags can often be produced relatively inexpensively, making them effectively disposable and reducing any need to sterilise them for re-use. In most tissue culture applications, aeration of the culture is essential in order to provide the cells with oxygen necessary for growth. In the past, methods such as sparging, surface aeration and medium perfusion have been used to increase oxygen availability. However, such methods can cause cellular damage, thereby severely limiting the efficiency of cell culture. Silicone rubbers have the highest oxygen permeability of known polymers, and tubing or membranes made from such materials are well-suited for use in cell culture, where they are able to provide improved diffusion of oxygen to the cells. Silicone rubbers not only provides gas permeability (including oxygen and carbon dioxide) but also vapour transmission, structural integrity, resilience and temperature resistance, all of which are desirable in cell and tissue culture. International patent application no. PCT/US96/20050 (Avecor Cardiovascular, Inc.) discloses a cell culture bag formed from a plurality of thin, spaced, gas-permeable silicone membranes, whose gas exchange rate is claimed to be significantly higher than most conventional culture bags. However, although such bags may be capable of sustaining higher cell densities and cell viability, they are ultimately limited by the surface area of the bag. Moreover, the interior surfaces of such bags are smooth and, thus, provide poor cell attachment features, making them unsuitable for efficient cell culture of anchorage-dependent cells. Furthermore, certain "problem" cell types are unable to attach to the smooth interior surface of the bags. An elaborate (and seemingly expensive) method of increasing the surface area available for cell adhesion is described in U.S. Pat. No. 4,937,194 (Baxter International, Inc.), which discloses a flexible bag containing an internal cellular structure, such as a honeycomb type structure with hexagonal channels passing through it, serving as adherent sites for cells being cultured. This document also proposes the use of microcarriers, such as small glass spheres or sodium alginate, to increase the surface area available for cell adherence inside the bag. There is a need, therefore, to overcome some of the aforementioned disadvantages. Accordingly, in an especially preferred embodiment of the invention in its fourth aspect, there is provided a culture chamber in the form of flexible bag or envelope. Such a culture bag provides an increased growth substrate surface area for cell attachment, as well as providing a growth substrate that will assist cell attachment. Moreover, the bag structure is simple and inexpensive to manufacture. In a preferred embodiment, the bag is made from at least one silicone rubber sheet that is coated with a silicone rubber layer having a rough or uneven micro-cupulated growth surface exhibiting a plurality of craters or crater-like depressions. Preferably, a room-temperature vulcanising silicone rubber precursor is used, whilst the sacrificial filler used to produce the textured surface is preferably sodium chloride. The textured or micro-cupulated surface so formed significantly increases the surface area for cell attachment, thereby increasing the efficiency of cell culture. The micro-cupulated surface also assists attachment and growth of certain "problem" cell types, such as, for instance, stromal cells necessary for stem cell expansion processes. Stromal cells originating from bone require a textured surface on which to grow if their proliferation is to be optimised. As already described above in relation to the culture chamber, the culture bag preferably also includes one or more ports, extending between the bag interior and bag exterior. Such ports may be used for introducing nutrient medium, taking samples, adding further ingredients, etc. The ports should preferably have valves, locks or the like, to avoid contamination of the big interior. In a preferred embodiment, the culture bag is provided with a inlet and an outlet port with luer locks, and a septum port for taking samples or introducing substances into the bag. The ports are desirably positioned between the sealed edges of the culture bag. It has been found that the application of a textured surface to a culture bag wall in accordance with the invention can result in the wall becoming opaque. In a preferred embodiment, therefore, the culture bag also includes at least one portion of membrane to which no textured surface layer has been applied, this area serving to act as a transparent window, thus allowing a user to see inside the culture chamber. In a further embodiment, the culture chamber also includes a valve means, allowing the release of gases that build up during cell growth and may form an air bubble inside the bag. The presence of a bubble within the chamber can prevent colonisation on the surface area adjacent the bubble because the surface will not be in contact with the culture medium. Thus, the presence of a valve in the culture chamber wall helps to minimise the size of any gas bubbles, thereby allowing a larger surface area of the bag to remain in contact with the nutrient medium and to be available for cell attachment. Almost complete colonisation on the interior chamber surface is, therefore, possible, increasing the efficiency of the culture chamber. Desirably, the valve comprises a filter means, allowing gases to diffuse out of the chamber but preventing microbial contamination. In a preferred embodiment, the valve means comprises one or more layers of a hydrophobic material, such as a hydrophobic PTFE membrane, preferably having a thickness of around 0.25 mm and a porosity of 0.2 microns. However, other suitable forms of valves means will also be apparent to those skilled in the art. The growth surface of the culture chamber or culture bag may be treated to further enhance cell adhesion, for example by charging the surface by bombardment with electrons. It is also possible to modify the free —OH groups of the silicone rubber surface to encourage attachment of various chemical moieties, in the manner already described in relation to the invention in its third aspect. Alternatively, cell attachment to the growth surface of the culture chamber may be promoted by adapting the size of the micro-cupules or depressions to the specific requirements of the cells to be cultured. In a preferred embodiment, the culture chamber further comprises a second chamber separated from the first chamber by means of a semi-permeable membrane. The second chamber preferably has an access means separate from that of the first chamber.

In a fifth aspect of the invention, there is provided an apparatus comprising a plurality of culture chambers according to the invention in its fourth aspect, for use in a method of culturing microbiological material. In an embodiment, the inlets of the culture chambers are interconnected and the outlets of the culture chambers are interconnected. In a preferred embodiment, the apparatus has at least one further chamber(s) having a semi-permeable wall that is positioned within each culture chamber, each semi-permeable chamber (s) having an inlet that is interconnected with the inlet of any other semi-permeable chambers and having an outlet that is interconnected with the outlet of any other semi-permeable chambers. In a preferred application, anchorage-dependent stromal cells are grown on the textured surface of the culture chamber(s), and anchorage-independent stem cells are then inoculated into the culture chamber(s), to allow proliferation of the stem cells. Preferably, the apparatus is a bio-reactor. The bio-reactor is particularly applicable to the bio-processing of liquors containing particular matter, such as blood cells or cell debris. Conventionally, bio-reactors are normally closed systems and, as such, have the disadvantages of relatively low productivity and efficiency. One particular drawback is the limited volume of oxygen available for reaction in such closed systems. Moreover, such systems not normally suitable for the processing of liquors containing particular matter, such as whole blood. The bio-reactor according to the invention does not suffer from the aforementioned problems because it comprises oxygen permeable walls, and a textured surface of silicone rubber to assist the growth process of the bio-substances. Thus, the desired product may be subsequently generated in a continuous process by a passage of liquid nutrient medium over the bio-substances. In a preferred embodiment, a method of carrying out a bio-processing operation in a culture chamber or an apparatus comprises attaching cells for performing the bio-processing function to the textured surface of the culture chamber(s), introducing liquor to be processed into the culture chamber(s) via an inlet and collecting the processed liquor at an outlet from the culture chamber(s). Preferably, the spent medium including cellular by-products is removed from the culture chamber(s), and fresh nutrient medium is passed through a semi-permeable chamber(s) located within the culture chamber(s), so to allow fresh medium to diffuse through the semi-permeable membrane into the culture chamber(s). Preferably, the nutrient medium is passed through the semi-permeable chamber in the opposite direction to that in which the liquor or spent medium is passed through the culture chamber. This has the advantage that cells growing in those areas of the culture chamber having the most heavily depleted medium are contacted with fresh medium first. The nutrient medium may be recycled. In a preferred embodiment, the apparatus is filled with liquid medium, which has first been inoculated with a desired cell line. The assembly of reactor tubes may then be arranged to be rotated or agitated, for example, using machinery such as that employed for conventional roller bottles. Rotation may be continued until cell confluence is obtained, as evidenced by the levelling of the rate of glucose uptake. The inner surfaces of the reactor tubes are, therefore, extensively coated with the cells at this stage. If appropriate, rotation may be interrupted for replacement of the medium in the reactor. The reactor tubes can then be removed from the rollers and connected to a suitable media reservoir. A continuous stream of liquid nutrient medium may be arranged to pass through the reactor envelopes, the product being harvested at the outlet. During this procedure, it is desirable to provide an airflow over the reactor, to assist oxygenation. In a preferred embodiment, the apparatus is especially adapted for bio-processing of liquors containing particulate matter, such as blood cells or cell debris. The continuous flow system according to the invention is especially applicable to the processing of whole blood, for example, in an artificial extra corporeal organ substituting or supporting the functions of the human liver. Advantageously, the system obviates the need of separating the particulate matter prior to processing and then having to reunite the constituents. It is also envisaged that the culture chambers and apparatus according to the invention may have other medical applications, such as for expansion of other primary cell types, or for use as an ex vivo model for drug metabolism if colonised with hepatocytes and the like. In another embodiment, the culture chambers further include semi-permeable chambers positioned within themselves, such as, for example, semi-permeable chambers made of cellulose acetate. These semi-permeable chambers are arranged to be separately connected to common inlets and outlets at their respective ends. In this embodiment, the bio-processing operation involves the following procedures. First, the cells grown to perform the bio-processing function are attached to the textured surface of the culture chamber. The culture medium is then removed from said culture chambers. Next, the nutrient medium is passed through the semi-permeable chambers, introduced from a reservoir through the inlet at one end of the semi-permeable chambers, issuing at the outlet on the opposing end. If desired, the medium may be recycled from the outlet, to return again to the inlet of the chambers. The liquid to be processed, such as blood, for example, is then arranged to flow through the culture chambers, the textured interior surface of which are now coated with cells. The liquor is introduced for this purpose at the inlet of the culture chambers, formerly serving at the medium inlet, and issuing at the outlet on the opposing end. The liquor is preferably passed through the culture chambers in opposing direction to that of the nutrient medium. During this procedure, nutrients from the medium pass through the semi-permeable chambers, traversing the stream of liquor, to feed the cells adhering to the coating of the culture chambers. At the same time, the semi-permeable chambers also perform the function of cleansing the liquor of waste materials, such as ammonia or urea, etc. The treated liquor is finally collected at the outlet of the culture chambers. The productivity and efficiency of the growth process, especially in the case of anchorage dependent cells, can be substantially enhanced using the bio-reactors according to the invention, especially when compared with conventional reaction vessels that do not utilise oxygen permeable containers and, thus, cannot sustain cell growth process in the manner permitted by the invention.

In a sixth aspect of the invention, there is provided a well for use in a method of culturing microbiological material having at least one wall defining the well, at least a portion of the wall being gas-permeable, to enhance oxygen supply to the well, and at least a portion of the interior surface of the wall being textured, to increase surface area and to enhance cell adherence. In a preferred embodiment, the gas-permeable portion of the wall and the textured portion of the wall are positioned at or near to the base of the well. In another embodiment, the gas-permeable portion of the wall comprises a gas-permeable membrane, preferably formed of silicone rubber. The membrane preferably has a textured surface facing the interior of the well, to increase available surface area and to facilitate cellular attachment. In a preferred embodiment, the textured surface has crater-like depressions or micro-cupules and is preferably a textured silicon rubber layer made by a method according to the invention in its second aspect. In a further embodiment, at least a portion of the interior surface of the wall comprises porous silicone rubber in accordance with the invention in its third aspect, preferably near the base of the well. In an especially preferred embodiment, the porous silicone rubber is provided with a textured silicone rubber layer which serves to form the interior surface of the well. Such wells are particularly useful in cellular assays which require the cells to remain substantially trapped in the wells, during a succession of steps involving washing or treatment with various reagents.

In a seventh aspect of the invention, there is provided a microtitre plate having at least one well according to the invention in its sixth aspect. The wells help to increase both the quantity of cells that can be grown in a microtitre well of a given size, as well as their metabolic activity. Preferably, the microtitre plate has at least one well having a wall at least a portion of which comprises a textured silicone rubber surface in accordance with the invention in its second aspect. As microtitre wells become increasingly minimized in size, the number of cells that can be grown in each well, for example, for drug metabolism studies, is also reduced because of the decrease in available growth surface area.

Moreover, those cells that can be grown are also starved of oxygen due to the decrease in gassing surface to volume ratio. The microtitre plate according to the invention helps to eleviate this problem by firstly increasing the available surface area with the textured surface and secondly allowing the cells to be gassed from below the second membrane.

In an eighth aspect of the invention, there is provided an implant device comprising a cell support structure having a coating with a textured surface, to promote anchorage of the implant by cell attachment and ingrowth by surrounding tissue upon implant. Preferably, the textured surface has crater-like depressions or micro-cupules. In an especially preferred embodiment, the coating comprises textured silicone rubber, preferably manufactured according to the invention in its second aspect. The implant devices according to the invention may take many different forms, such as, for example, a heart valve, a sternum implant, or a reconstructed calf ligament. The textured surface on the implants acts as an anchor for tissue in-growth. Thus, the textured implant can help to prevent migration of larger implants or to promote a secure bond, where the interface with the implant and the surrounding tissue is critical. It has been found that the textured surfaces according to the invention have the further advantage of helping to reduce the formation of capsule-type scar tissue following implantation.

In a ninth aspect of the invention, there is provided a substrate for growth of skin grafts in vitro comprising a flexible membrane having a textured surface. A major problem associated with the growth of skin ex vivo is that, when it is grown on a rigid or solid surface, the skin tends to be bristle and does not have the opportunity to "learn" to be flexible. In addition, the undersurface of the skin tends to be smooth and scar-like, which makes it difficult for the skin graft to take. The flexible membrane used in the inventive substrate helps to prevent the skin graft from becoming brittle, whilst the textured surface increases the surface area available for cell adhesion, promotes cell adhesion and helps to gives the skin a rough surface, so as to enhance "taking" of the graft on transplant. In an embodiment, the flexible membrane is gas-permeable, preferably comprising a material such as silicone rubber. In a preferred embodiment, the textured surface has crater-like depressions or micro-cupules. Preferably, the textured surface is formed of silicone rubber manufactured according to the invention in its second aspect. The textured surface not only provides a greater surface area for cell growth, but also allows a degree of ingrowth into the silicone rubber in small areas, so that upon removal from the growth surface, the skin undersurface will be textured, assisting the taking process of the graft. In addition, the high oxygen permeability of the silicone rubber would assist in promoting the metabolic activity of he growing graft.

In a tenth aspect of the invention, there is provided a tissue support structure for use in a method of culturing tissue or cellular agglomerates, which comprises a biocompatible material having an internal system of pores, the pores promoting cell attachment and anchorage and oxygen supply to the tissue. Microparticles of organs grown ex vivo have many applications in the drug development industry. However, conventional support substrates for tissues or tissue fragments grown ex vivo are severely limited as to the size of the tissue agglomerates that may be grow. The need to provide oxygen and nutrients to the centre of a three dimensional tissue mass has been widely recognised by those skilled in the art and has been addressed in a number of different ways, all of which involve complex and expensive support structures having specific structural features for gas and nutrient supply. The tissue support structures according to the invention have a system of pores and channels within the porous structure that is capable of mimicking a biological capillary system, delivering oxygen directly to the centre of the tissue growing on the structure. This allows much larger agglomerates to be formed while avoiding necrosis and apoptosis. In a preferred embodiment, the porous material is provided with small, fine bore tubes. In another embodiment, the shape of the porous material may be adapted so as to engineer the shape of the resultant tissue. In a preferred embodiment, the porous material comprises porous silicone rubber, preferably made according to the invention in its third aspect. In an especially preferred embodiment, the tissue support structure comprises porous silicone rubber having small, fine bore tubes. In this case, the silicone rubber may be provided with a porous and micro-capillary structure by using finely ground sacrificial filler and long thin needles of crystalline sacrificial filler in admixture in the process according to the invention in its third aspect, the ground filler serving to provide the porous superstructure and the needles of filler serving to provide the micro-capillaries. However, artificial capillaries may also be introduced into the porous silicone rubber by other methods, such as trapping gases in the setting silicone rubber, mechanical disruption, laser ablation, etc.

In an eleventh aspect of the invention, there is provided an apparatus for culturing tissue or cellular agglomerates comprising a tissue support structure according to the invention in its tenth aspect and a gas-permeable membrane, to enhance oxygen supply to the system of pores and channels within the porous material, and therefore to the tissue. Preferably, the gas-permeable membrane is attached to the porous material. In a preferred embodiment, the gas-permeable membrane is a silicone rubber, preferably made in accordance with the invention in its third aspect. Preferably, the porous material is attached to the gas-permeable membrane using a gas-permeable adhesive, such as a silicone rubber adhesive. In a preferred embodiment the plurality of tissue support structures are arranged in close proximity to one another, so as to allow fusion between tissue or cell masses growing on each structure, to create larger tissue or cellular agglomerates. It is envisaged that tissue grown on this type of structure could reach macro-dimensions being fed with oxygen via diffusion through solid threads attached to tubes through which oxygen would be passed. Preferably, the support structure is in the form of a pillar, the dimension of which are approximately 0.25 mm×2 mm.

In a twelfth aspect of the invention, there is provided an artificial implant formed from a material having an increased system of pores, the pores promoting cell attachment and anchorage and oxygen supply to the cells on the implant surface. The pores throughout the structure allow a degree of ingrowth and anchorage of the cells, as well as a pathway for supply of oxygen to the cells on the surface. In a preferred embodiment, the porous material comprises porous silicone rubber, preferably made according to the third aspect of the invention. In a preferred embodiment, the artificial implant is adapted for use as a cartilage implant. In such applications, the porous silicone rubber is carefully selected to contain the necessary degree of biologically inert filler to give it the required degree of elasticity and/or flexibility of the cartilage. Preferably, the porous material is seeded in vitro with chondrocites, to form a layer of cartilage over the implant. Such an implant may be used for replacing eroded joints and the porous silicone structure may be moulded to conform to the shape of the bone it is to protect. Prior to the present invention, cartilage intended for such purposes was grown in vitro in a flat single layer on culture plates and was then placed over the eroded bone. The principle disadvantage of such a method is that the cartilage so grown is in a flat form and does not readily accommodate to the contours of the bone to be protected. The implants according to the invention do not suffer from such a disadvantage and, thus, may be used to provide "spare parts" for surgery in the human body. In another preferred embodiment, the porous material of the cartilage implant could be moulded into the shape of a nasal bridge, or an ear. This type of permanent synthetic bio-compatible implant offers both support and a degree of permanent protection to the cartilage structure.

In a thirteenth aspect of the invention, there is provided an artificial implant according to the invention in its twelfth aspect in the form of a vascular graft. Conventional vascular grafts often suffer an adverse fate because their base material has incompatible physical properties to those of the native tissue. In a preferred embodiment, the vascular graft of the present invention comprises a hollow tube made from porous material, preferably porous silicone rubber. In an embodiment, the interior surface allows cell adhesion, and preferably endothelial cells are grown on the interior surface of the graft. In another embodiment, the exterior surface also allows cell adhesion, and preferably smooth muscle cells are grown on the exterior surface of the graft. In a preferred embodiment, one or both surfaces of the graft are additionally roughened to enhance cell attachment, preferably by providing the graft with textured silicone rubber surface. The elastic, compression and oxygen transport characteristics of porous silicone rubber closely mimic those of living tissue and, thus, help permit common problems, such as stenosis, to be overcome. A further advantage associated with the vascular grafts according to the invention are that these produce a lamina flow and not the turbulent flow associated with rigid synthetic grafts, hence helping to minimizing the problems of thrombosis. Due to the chemical properties of silicone rubbers, such vascular grafts would also be resealable, which would be advantageous for patients requiring repeated vascular access, for example, patients suffering from renal disease and undergoing long-term kidney dialysis.

In a fourteenth aspect of the invention, there is provided a cell implant means comprising a porous material for retention of cells to be implanted, the pores promoting cell attachment and anchorage and oxygen supply to the cells, and a protective means to shield the cells from immune attack after implant. In an embodiment, the porous material comprises silicone rubber, preferably made by the method according to the invention in its third aspect. In a preferred embodiment, the protective means desirably comprises a semi-permeable membrane forming an envelope around the porous material. In an especially preferred embodiment, the cell implant means is adapted for use as an endocrine implant. The porous material is seeded in vitro with endocrine cells, such as islets of Langerhans cells. The development of fully-functional endocrine implants, especially of the islets of Langerhans insulin-secreting cells, has long been a target for clinical research. However, expanding islet cells has proved extremely challenging, because it is difficult to make them proliferate in culture. Islet cells from foetal tissue have been proliferated in culture but permanently lose function over time. The endocrine implants according to the present invention should help to overcome such difficulties. On implantation of the endocrine implant, the required hormone is released through the semi-permeable membrane, whilst this membrane also acts as a barrier to the body's own defences against the foreign cells. Regulation of the hormones released can occur naturally, as feedback control molecules are able to pass through the semi-permeable membrane and communicate with the endocrine cells directly.

In a fifteenth aspect of the invention, there is provided a drug delivery system comprising a porous material whose pores have been impregnated or saturated with a drug for delivery. Preferably, the drug delivery is suitable for implantation into a human or animal body. In a preferred embodiment, the drug is present in admixture with at least one sustained release ingredient. In an especially preferred embodiment, the porous material comprises a porous silicone rubber, preferably made by a method according to the invention in its third aspect. Many drugs exist as small molecules which are capable of diffusing readily through silicone rubber. Such drugs can be incorporated into the porous silicone rubber, which acts as a drug delivery system. Advantageously, the porous nature of the silicone rubber means that it is capable of exposing a large surface area to bodily fluids for a relatively small implant. Moreover, the synthetic nature of the silicone rubber means that the system is less likely to be rejected by the body when implanted. In addition, the material will not biodegrade as with many of the current devices, making it possible to explant the spent device for analysis and monitoring purposes if required.

In a sixteenth aspect of the invention, there is provided a filtration media comprising porous silicone rubber, for use in separations. Preferably, the porous silicone rubber is made according to the invention in its third aspect. In a preferred embodiment, the pores of the silicone rubber are of sub-micron size, preferably in the order of 1 nm–10 $\mu$m, more preferably in the order of 10 nm–5 $\mu$m, and more preferably about 0.1–0.5 $\mu$m. The filtration media may be used in magnetic separation and, in such a case, the porous silicone rubber preferably includes magnetic additives. The filtration media may also be used in expanded bed adsorption and, for this application, the porous silicone rubber is preferably in particulate form. The filtration media may be for use in static inline filtration, for which the porous silicone rubber is preferably in the form of sheets or tubes. In a preferred embodiment, the filtration media comprises porous silicone rubber in the form or annular discs. Preferably, porous silicone rubber with a sub-micron pore size is used. In particulate form, the filtration media according to the invention is highly suited for use in the burgeoning market of expanded bed absorption technology. This is because porous silicone rubber can be easily modified to have the appropriate density and, due to its elastic nature, can be used in whole broth or continuous processes over protracted periods of time. After primary processing, the filtration media can be made receptive to all common moieties used in affinity chromatography processes. In addition, the filtration media according to the invention can also easily be made magnetic, so that it can be easily separated from a whole broth system using magnetic separation.

In a seventeenth aspect of the invention, there is provided a cell cryopreservation system comprising a porous material for absorbing cell culture into the internal system of pores and a container suitable for storage in liquid nitrogen. In a preferred embodiment, the porous material comprises porous silicone rubber, preferably porous silicone rubber made in accordance with the invention in its third aspect. The container preferably comprises releasable sealing means. In an alternative embodiment, the container is a syringe-type plunger. In such an embodiment, a number of cylindrical particles of porous silicone rubber may be placed in a tube fitted with a syringe type plunger. An operator could then suck up the required culture to saturate the porous silicone rubber particles and then store the device in liquid nitrogen. Upon retrieval, the operator then has a number of porous silicone rubber particles containing the same culture that can be used for several inoculums.

In an eighteenth aspect of the invention, there is provided an electrode comprising a porous material having electrically conductive particles dispersed therein. In a preferred embodiment, the porous material comprises porous silicone rubber, preferably a porous silicone rubber made in accordance with the invention in its third aspect. Preferably, the conductive particles are metal or carbon powders. In another embodiment, the porosity of the electrode material promotes adherence of microorganisms to the electrode surface. In an especially preferred embodiment, the microorganisms are capable of digesting waste, such that the electrodes may be used in the treatment of sewage and in similar applications. In another embodiment, the electrode forms part of an electrode system comprising a plurality of electrodes immersed in a liquid electrolyte and connected to an electric circuit. As in conventional electrolytic systems, in use, two electrodes (a cathode and an anode) are immersed in the liquid electrolyte, are connected to an electric circuit with a potential being applied between them. In special applications, electrolytic baths may comprise a plurality of electrodes. The porous silicone rubber electrodes have a number of advantageous features, including a large surface area and, hence, a high electrical capacity, robustness, inertness and resilience (aided by some degree of elasticity). Such characteristics are particularly important in the relatively hostile chemical and physical environment of agitated liquid electrolytic cells. Furthermore, the porous silicone rubber also provides a favourable surface for the growth of micro-organisms making such electrodes particularly suitable for special uses in water purification and sewage treatment applications. Traditionally, such water treatments normally comprise the functions of converting (a) carbonaceous material to carbon dioxide and water, (b) nitrites to nitrates, and (c) nitrates to atmospheric nitrogen, all three functions relying on the actions of micro-organisms. Among difficulties associated with conventional procedures are those of providing an adequate stream of oxygen through the sewage to maintain the micro-organism activity. This usually requires agitation of the liquid using mechanical stirrers, while passing a stream of oxygen through the sludge in the case of functions (a) and (b) and providing a safe reducing atmosphere for (c). Using porous silicone rubber electrodes according to the invention in, for example sewage treatment, advantages are achieved in respect of greater output efficiency, enhanced reliability owing to the absence of moving parts in the system, as well as lower operating costs. By using the porous silicone rubber electrodes, an oxygen stream is applied at the anode to pass through the sewage, allowing micro-organisms to effect the reactions (a) and (b), while an enhanced level of hydrogen at the cathode aids the conversion by micro-organisms of (c).

In a nineteenth aspect of the invention, there is provided a wound dressing comprising a first layer of a porous gel and a second layer of a carrier gel. In a preferred embodiment, the porous gel layer comprises a porous silicone rubber gel, preferably made by a method according to the invention in its third aspect. The carrier gel layer may also comprise a silicone rubber gel. Preferably, the carrier gel is applied to a supportive structure, such as a Dacron® mesh. In a preferred embodiment, the porous gel layer is infused with a drug for delivery to the wound, such as a growth-promoting drug or an antibiotic. The silicone rubber wound dressing according to the invention also helps to control scar formation by leaching low molecular weight silicones into the wound, a technology already employed in the field. The silicone rubber wound dressing has the added advantage of increasing the contact area with fluids from the wound, thereby improving leaching and allowing greater oxygen transport to the site, whilst maintaining asepsis. Moreover, the dressing permits drugs infused into the porous structure to leach into the wound over a prolonged period of time to aid the healing process.

In a twentieth aspect of the invention, there is provided a clinical swab comprising a porous material, the pores increasing the surface area of the swab and promoting oxygen transport to the swab surface. In a preferred embodiment, the porous material comprises porous silicone rubber, preferably made by a method according to the invention in its third aspect. In a further embodiment, the porous material contains a radio-opaque additive, such as barium sulphate. This allows any lost swabs to be easily traced and then removed. In another embodiment, the porous material is infused with a drug. The swab is preferably attached to the end of a stick made, for example, of wood or plastic. The swab according to the invention has a number of advantages over the conventional swabs. The porous silicone rubber is oxygen permeable. The silicone rubber is also non-limiting, reducing the risk of debris being left behind after use. The silicone rubber is also better attached to the stick than cotton wool in conventional swabs. The silicone is furthermore chemically very stable and will also allow microorganisms to adhere to the swab surface.

BRIEF DESCRIPTION OF THE DRAWINGS

In order that the invention may be better understood, examples of the various aspects will now be described, by way of illustration only and with reference to the accompanying drawings, wherein:

FIG. 5 is a schematic plan view of a culture bag in accordance with the fourth aspect of the invention;

FIG. 6 is a schematic cross-sectional view of the culture bag of FIG. 5;

DETAILED DESCRIPTION OF THE INVENTION

Figure 1:
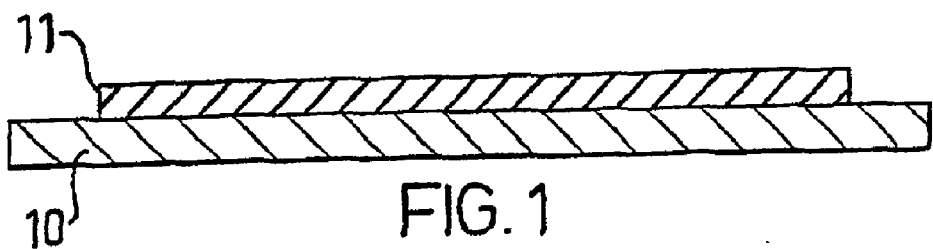
FIGS. 1, 2 and 3 show successive steps of the manufacturing process in accordance with the second aspect of the invention.
Figure 2:
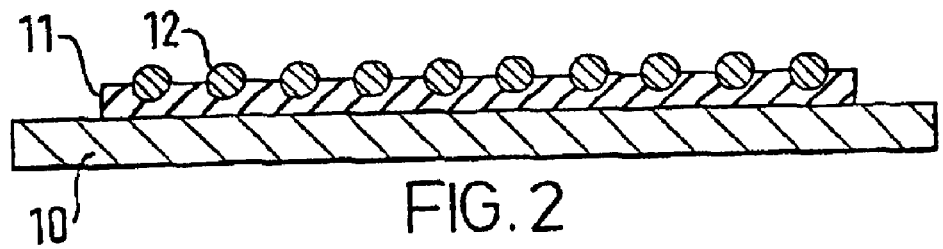
Figure 3:
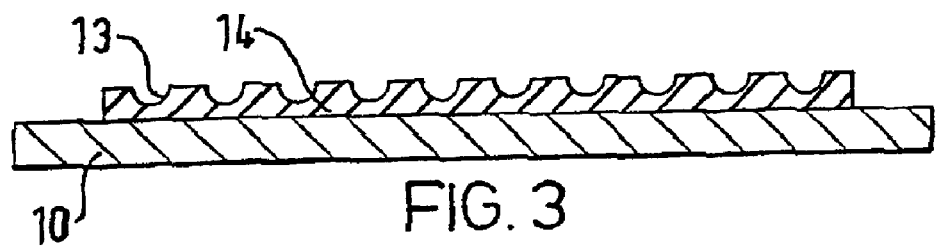

FIGS. 1, 2 and 3 show successive steps of the manufacturing process in accordance with the second aspect of the invention. In FIG. 1, the surface of a substrate 10 is coated with a layer of uncured silicone rubber precursor 11. In FIG. 2, a sacrificial filler 12, such as sodium chloride, is applied to the silicone rubber layer 11 whilst the latter is still tacky, the sodium chloride 12 becoming adhered to and partially embedded in the silicone rubber layer. Any excess sodium chloride 12 that is not adhered to the silicone rubber layer 11 is removed and the silicone rubber layer 12 is allowed to cure. Once the silicone rubber layer 11 has been cured, the sodium chloride 12 is dissolved in a solvent, such as water, leaving craters or micro-cupules 13 forming a textured surface structure 14 as shown in FIG. 3.

Figure 4:
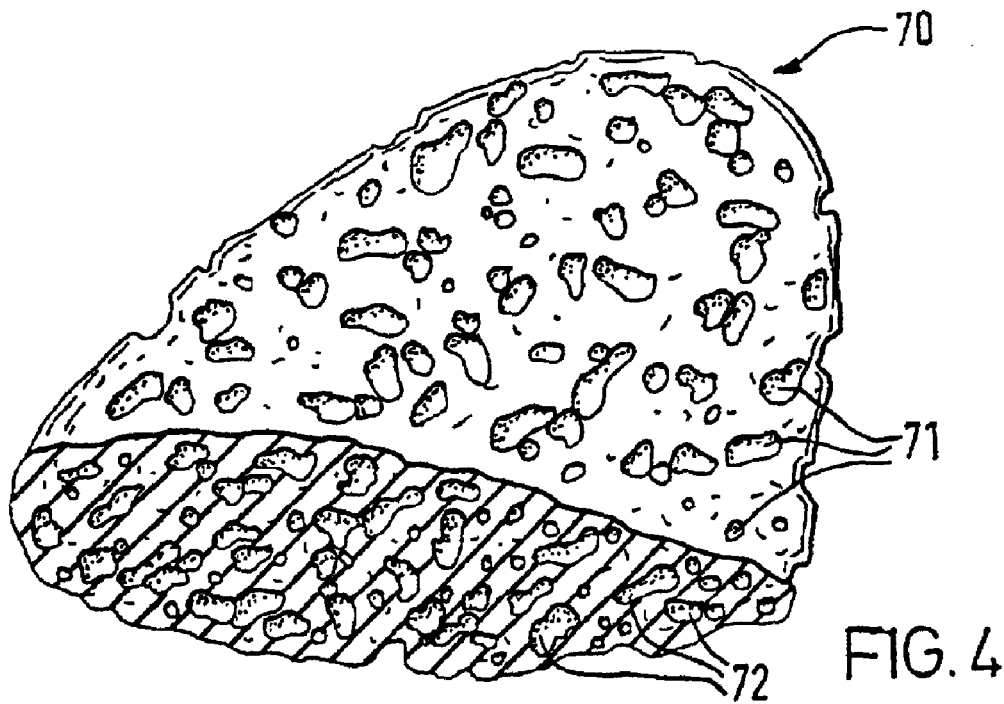
FIG. 4 shows a cross-sectional view of three-dimensional porous silicone rubber in accordance with the third aspect of the invention.

In FIG. 4, a porous silicone rubber article 70 has a textured exterior surface with craters 71 and pores 72 within the body of the silicone rubber article 70, forming porous channels throughout the three dimensional structure. The porous silicone rubber article 70 is made from GE Silicone's LIM 6070-D2 (part A & B) or McGhan NuSil's MED 4970 (part A & B), to form the silicone rubber and J. Astley & Sons Food Grade $NaHCO_3$ (sodium bicarbonate) as sacrificial filler. Stainless steel powder (MBC Metal Powders Ltd 316L SS fines 325 mesh) is also added for a high density silicone rubber product. The sodium bicarbonate is mixed with each of parts A and B of the silicone rubber separately, at a ratio of 3:1 w/w. The mixing is carried out using a conventional Z-blade mixer, although other mixer types may be used, or mixing may even be performed by hand. Stainless steel powder is added to a level to give the desired density (although other high mass powders, such as titanium oxide, can also be used). Once mixed with the sodium bicarbonate, parts A & B are stored separately in a cool place for further processing. The components must be kept apart as one contains the accelerator and the other the catalyst that will cause curing. If cross-contamination of the parts occurs, the material will start to cure. When ready to cure the material into the required shape, parts A & B are mixed together on a two roll mill for 15 to 20 minutes to ensure complete mixing. The resultant mixture is then fed into a cold head extruder and extruded through a die of the appropriate shape. The resultant extrudate is picked up by a heat resistant conveyor and passed through a hot box set to such a temperature that the extrudate itself is heated to 175° C. This facilitates the cure of the material without allowing the sodium bicarbonate to decompose and hence "blow" the material. Depending upon the geometry of the extrudate, it is passed through either a rotary cutter (for small cross-sections) or a reciprocating cutter (for larger geometries) and chopped into the appropriate particulate shape. This "preform" is the stored in a dry place until further processing is required. When required, the material is boiled in at least a five-times excess of pyrogen-free water for one hour. This process is repeated four or five times or until no further traces of sodium bicarbonate are evident, as indicated by the pH of the water. The material is then finally rinsed in pyrogen-free water, bottled in an excess of the same and autoclaved to facilitate sterile storage. The material is now in a form ready for sale as a stand alone support matrix.

In a further example, the porous silicone rubber article 70 is made GE Silicone's RTV (room temperature vulcanising) 615 (part A & B), as the silicone rubber material, and J. Astley & Sons Food Grade $NaHCO_3$ (sodium bicarbonate), as the sacrificial filler. For a high density silicone product, iron oxide (magnetic precipitate) from Fishers Scientific Products is used. The sodium bicarbonate is wet milled under xylene using a Biaton bead mill to a particle size of 0.1 to 0.4 $\mu$m. This range can be further narrowed by separation in a Malvern® particle sizer. Using these methods, a whole range of particle sizes and distributions can be achieved. The sodium bicarbonate is mixed with each of parts A and B of the silicone rubber separately, at a ratio of 3:1 w/w. The mixing is carried out using a conventional Z-blade mixer, although other mixer types may be used, or mixing may even be performed by hand. If the density is to be increased, the iron oxide is added to a level to give the desired density. Other high mass powders such as titanium oxide can also be used. Further weighting or magnetic moieties may also be mixed in, if required. Once mixed with the sodium bicarbonate, the parts A & B are stored separately in a cool place for further processing. When ready to cure the material into the required shape, parts A & B are mixed together on a two roll mill for 15 to 20 minutes to ensure complete mixing. Again other apparatus could be used. The resultant mixture is then fed into a cold head extruder and extruded through the open scroll and collected as ingots on trays. The ingots are then cured at 150° C. in a standard convection oven. The ingots are then ground in a mill to the required size and can again be sized using a Malvern® particle sizer if required. This "preform" is the stored in a dry place until further processing is required. When required, the material is boiled in at least a five-times excess of pyrogen-free water for one hour. This process is repeated four or five times or until no further traces of sodium bicarbonate are evident, as indicated by the pH of the water. The material is then finally rinsed in pyrogen-free water, bottled in an excess of the same and autoclaved to facilitate sterile storage. This product is biocompatible, it has pores in a very well defined size range and of an amorphous geometry.

Figure 7:
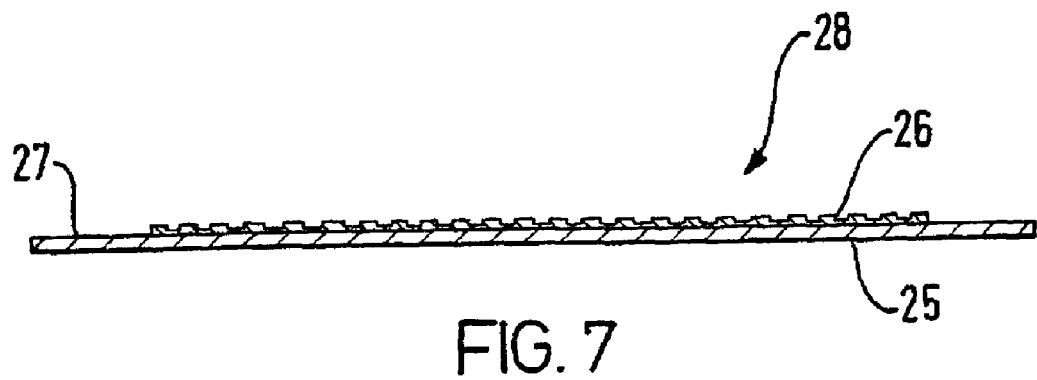
FIG. 7 is a cross-sectional view of a membrane wall of the culture bag of FIGS. 5 and 6.
Figure 8:
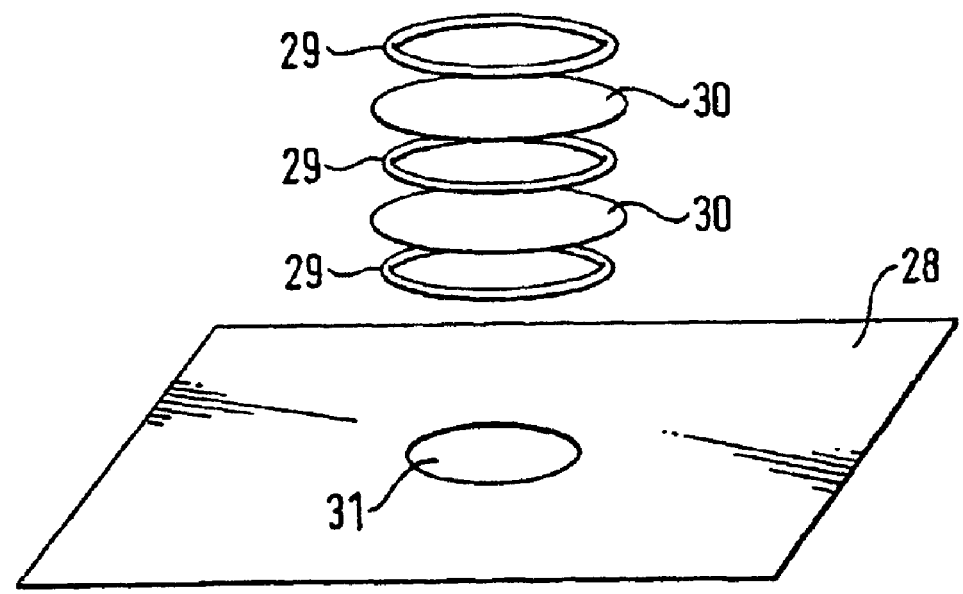
FIG. 8 is an exploded view of the valve of the culture bag of FIGS. 5 and 7.

In FIGS. 5 and 6, a culture bag 20 comprises two membranes 28 joined at their outer edges 27, each membrane 28 having a textured (interior) surface 26. Inlet and outlet ports 23 extend between the inside and the outside of the bag, each port 23 being provided with a valve 24. A degassing valve 22 is provided in the centre of one of the membranes 28, this membrane 28 being uppermost when the bag 20 is in use. In FIG. 7, each bag membrane 28 is prepared by covering the edges 27 of a smooth silicone rubber sheet 25 with a mask (not shown) and applying a layer of room-temperature vulcanising liquid silicone rubber to the exposed central portion of the sheet. Next, vacuum-dried salt is sprinkled over the layer of liquid silicone rubber so that it is uniformly covered. The liquid silicone rubber is then cured and the salt is washed out, producing a membrane 28 with a cratered or micro-cupulated surface 26. In FIG. 8, a degassing valve is formed by first cutting a hole 31 out of the centre of one of the membranes 28, over which the valve will be placed. A washer 29 made of uncured silicone rubber is positioned around the hole 31 on the smooth (outer) face of the membrane 28. A hydrophobic PTFE membrane 30 with 0.2 $\mu$m pores and a thickness of 0.25 mm is laid over the washer 29, and a second washer 29 is placed on top. This is then repeated with a second PTFE membrane 30 and a third washer 29. When the bag 20 is to be assembled, the two silicone rubber membranes 28 are laid on top of one another, with the rough surfaces together. Two lengths of tubing for the inlet and outlet ports 23 are placed between the silicone rubber membranes 28, protruding slightly into the rough area. The ports 23 are provided with valves 24. Next, room temperature vulcanising silicone rubber is applied to the untreated, smooth edges 27 of the silicone membranes 28, along which the membranes 28 are to be joined to form a bag configuration 20. Uncured silicone rubber is applied around the tubing where it lies adjacent to the smooth edges of the membranes 28. The constituents of the culture bag 20 so arranged are then welded or glued together using elevated temperatures and pressure. The edges of the silicone membranes 28 are sealed to form a bag 20, the degassing valve is formed from the layers of washers 29 and PTFE membrane 30, and the tubing for the ports 23 becomes integrated into the bag structure 20.

Figure 9:
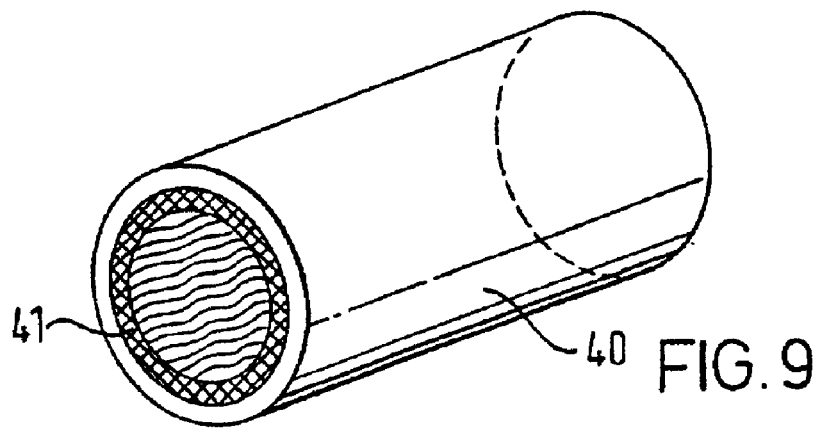
FIG. 9 is a diagrammatic illustration of a bio-reactor apparatus according to the fifth aspect of the invention.
Figure 10:
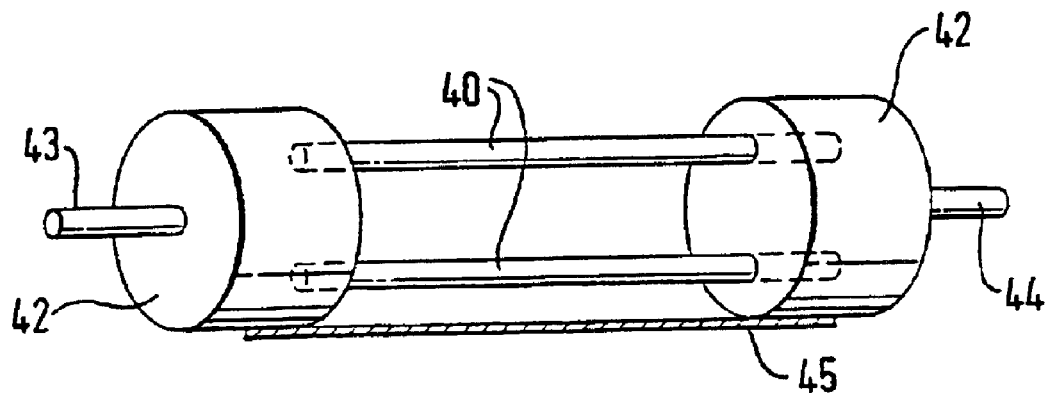
FIG. 10 is a silicone rubber tube from the bio-reactor of FIG. 9.
Figure 11:
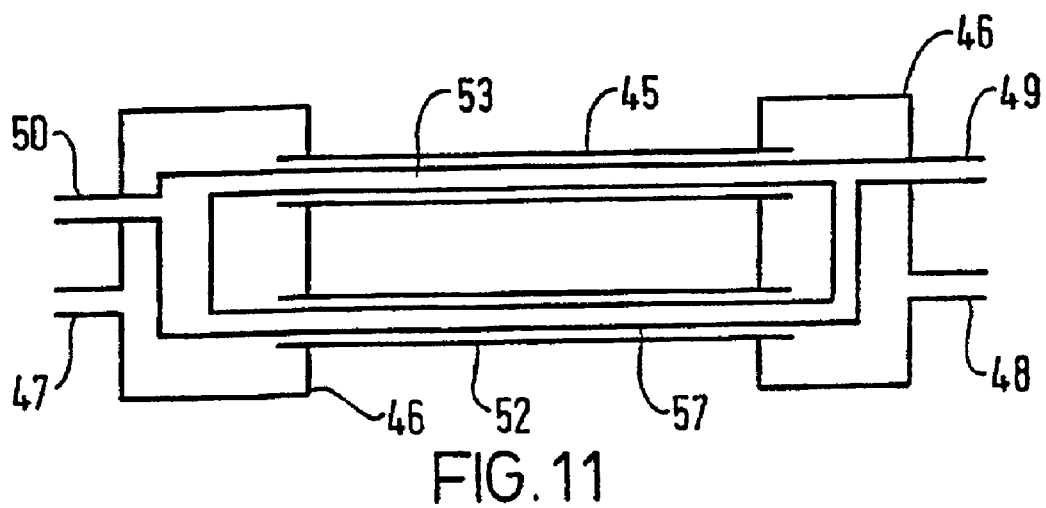
FIG. 11 is a cross-sectional side view of a bio-reactor apparatus with dialysis tubes.

In FIG. 9, a bio-reactor apparatus comprises two reactor tubes 40 (in practice, a larger number, such as seven or eight tubes, is generally preferred). Each reactor tube 40 carries an internal coating of textured silicone rubber 41. In use, in order to grow the cells on interior surfaces 41 of tubes 40, medium carrying cell lines is introduced through an inlet 43. Reactor tubes 40 are interconnected through distributors 42. One or more strengthening members 45 ensure rigidity of the assembly. The assembly is rotated on rollers (not shown), followed by evacuation of the liquid and subsequent passage of nutrient medium over the cells. The medium is introduced through the inlet 43 and issues from the outlet 44. The product is finally collected at the outlet 44. In FIG. 10, the reactor comprises a non-porous silicone rubber tube 40 carrying an internal coating of textured silicone rubber 41. In FIG. 11, dialysis tubes 51 are co-axially positioned within the reactor tubes 40. Cells are grown in the annular space 52 by the passage via introduction of medium comprising the cell line through the inlet 47. After removal of the liquid from the annular space through the outlet 48, the nutrient medium is passed through the dialysis tubes 51 via medium inlet 49, issuing at outlet 50. At the same time, the liquor to undergo the bio-reaction is passed through the reactor tubes via inlet 47, for collection at outlet 48.

Figure 12:
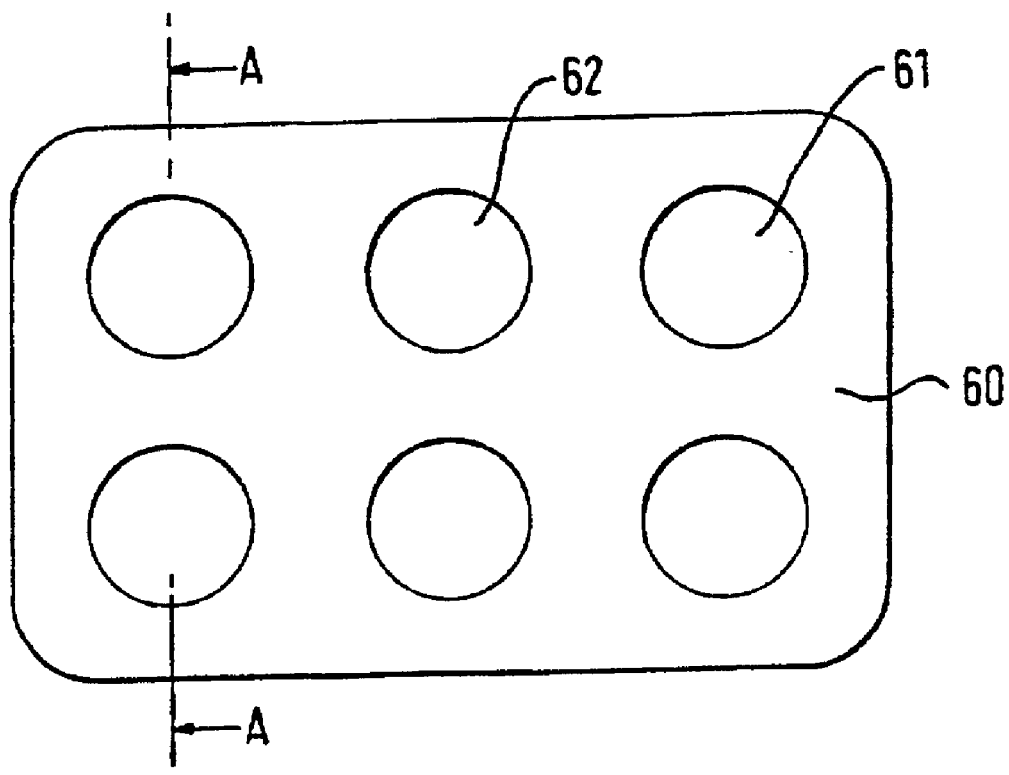
FIG. 12 shows plan view of a microtitre plate according to the sixth aspect of the invention.
Figure 13:
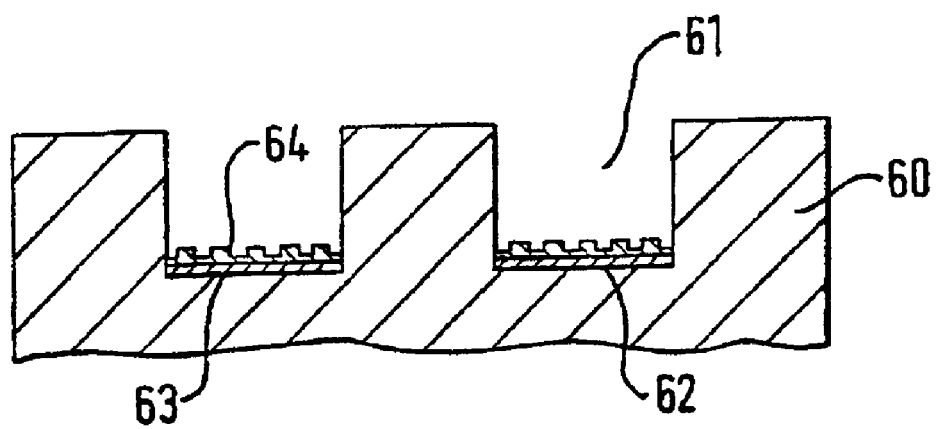
FIG. 13 shows a cross-sectional view of the plate of FIG. 12 along line A-A'.

In FIGS. 12 and 13, a standard microtitre plate 60 has wells 61 without base walls (either conventional microtitre plates are used and the base walls of the wells removed, or a microtitre plate is produced without any base walls). A non-porous silicone membrane 62 is attached to the bottom of the wells, the membrane comprises a silicone rubber sheet 63 having a coating with a textured surface 64 facing the area defined by the wells.

Figure 14:
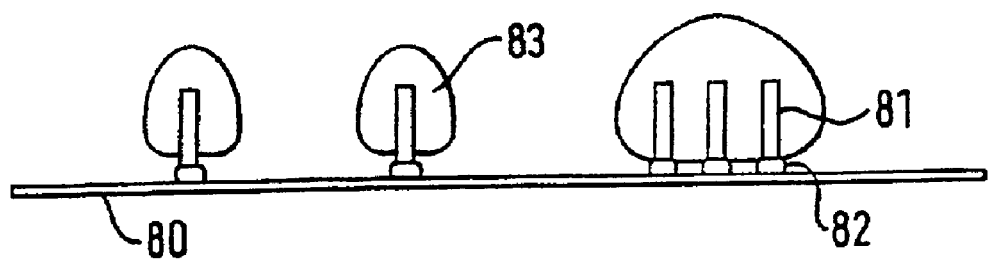
FIG. 14 shows a schematic artificial capillary system, in accordance with the ninth aspect of the invention.

In FIG. 14, a tissue growth support structure comprises a tissue mass 83, such as HT-29 (intestinal carcinoma) cells grown on pillars of porous silicone rubber 81, the pores acting as a capillary system, supplying oxygen to the cells in the centre of the tissue mass 83. The pillars 81 are attached to a gassing membrane 80 in a bio-reactor configuration, using gas permeable silicone rubber adhesive 82. The oxygen diffuses through the gassing membrane 80 and through the system of pores and channels to reach the tissue agglomerate 83. The tissue growth support structure permits much higher densities of HT-29 cells than conventional systems.

Figure 15:
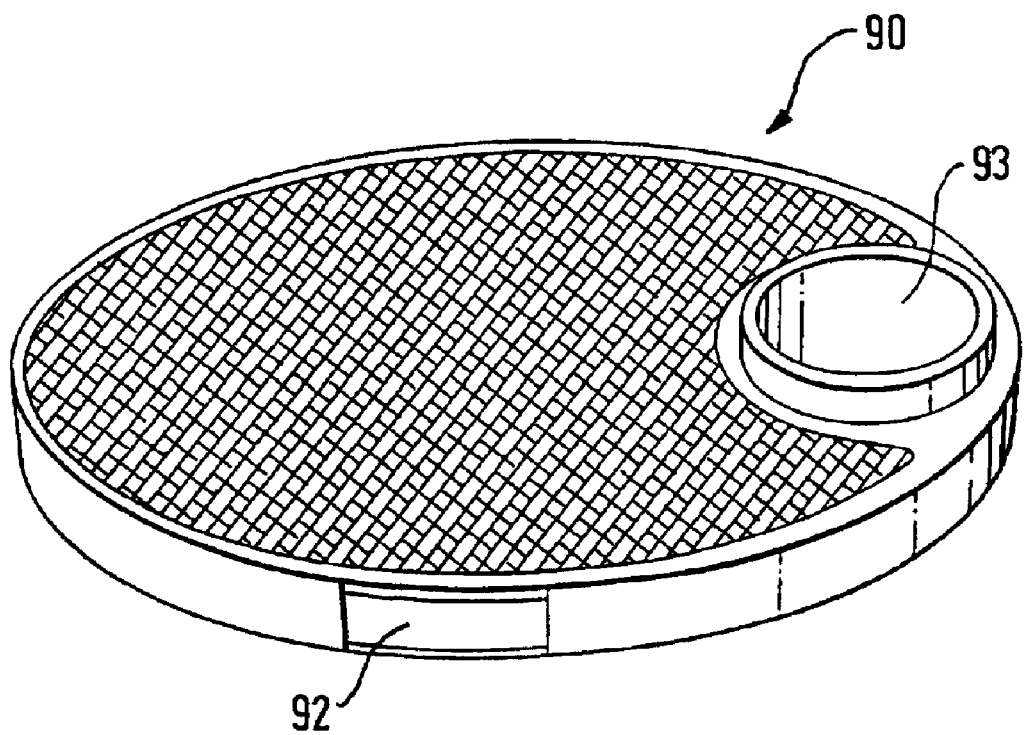
FIG. 15 shows a part cross-sectional view of an endocrine implant according to the thirteenth aspect of the invention.

In FIG. 15, islet of Langerhans cells are immobilized within a bio-wafer 90 consisting of a disc of porous silicone rubber 92, in which the islet cells are attached, sandwiched between semi-permeable membrane layers 91, which allow insulin out but stop host immune cells from attacking and destroying the transplanted islet cells.

What is claimed is:

1. A porous silicone rubber article having a structure adapted for growth of cells or living tissue obtained by a method comprising mixing a biologically acceptable sacrificial filler with a silicone rubber precursor, curing the resultant mixture at a temperature below 180° C., and removing the sacrificial filler by dissolution to form a porous silicone rubber article, said sacrificial filler is an inorganic salt that has been ground, and said inorganic salt is selected from the group consisting of metal halides, metal carbonates and metal bicarbonates.

2. A biomedical device comprising a porous silicone rubber article as claimed in claim 1.

3. A method of making a silicone rubber article having a structure adapted for growth of cells or living tissue, which comprises mixing a biologically acceptable sacrificial filler with a silicone rubber precursor, curing the resultant mixture at a temperature below 180° C., and removing the sacrificial filler by dissolution to form a porous silicone rubber, said sacrificial filler is an inorganic salt that has been ground, and said inorganic salt is selected from the group consisting of metal halides, metal carbonates and metal bicarbonates.

4. A method as claimed in claim 3, wherein the silicone rubber precursor can be cured or vulcanized at room temperature.

5. A method as claimed in claim 3 or 4, wherein the biologically-acceptable sacrificial filler is bio-compatible, such that it is innately non-toxic and does not leave a toxic residue.

6. A method as claimed in claim 3 or 4, wherein the sacrificial filler does not interact chemically with the silicone rubber precursor or with the resultant silicone rubber and is stable at temperatures used to cure the resultant mixture.

7. A method as claimed in claim 3 or 4, wherein the sacrificial filler is granular.

8. A method as claimed in claim 3 or 4, wherein the sacrificial filler is amorphous.

9. A method as claimed in claim 3, wherein the sacrificial filler is milled to a particle size of 0.01–10 $\mu$m.

10. A method as claimed in claim 3, wherein the sacrificial filler is milled in an organic solvent.

11. A method as claimed in claim 3, wherein the inorganic salt is selected from the group consisting of lithium bicarbonate, sodium bicarbonate, potassium bicarbonate, lithium chloride, sodium chloride and potassium chloride.

12. A method as claimed in claim 11, wherein the sacrificial filler is sodium bicarbonate or sodium chloride.

13. A method as claimed in claim 12, wherein the sodium bicarbonate or sodium chloride is wet-milled under xylene.

14. A method as claimed in claim 3, wherein the sacrificial filler is removed by dissolution.

15. A method as claimed in claim 3, wherein the sacrificial filler does not cause swelling of the silicone rubber when removed using an aqueous solvent.

16. A method as claimed in claim 15, wherein the sacrificial filler is sodium bicarbonate.

17. A method as claimed in claim 3, wherein free —OH groups of the silicone rubber are chemically modified, so as to enhance cell adherence.

18. A method as claimed in claim 3, wherein the surface of the silicone rubber is charged by bombardment with electrons.

19. A method as claimed in claim 3, wherein the silicone rubber precursor comprises at least one additive that is not removed with the sacrificial filler and serves to impart desired physical properties to the rubber.

20. A method as claimed in claim 19, wherein the additive is a metal powder or carbon black and serves to render the silicone rubber electrically conductive.

21. A method as claimed in claim 20, wherein the additive is stainless steel powder.

22. A method as claimed in claim 20, wherein the additive is iron oxide.

23. A method as claimed in claim 19, wherein the additive is an inert substance, and serves to render the silicone rubber mechanically rigid.

24. A method as claimed in claim 3, wherein a surface of the silicone rubber precursor is contacted with the sacrificial filler, so as to form a structured silicone rubber having a textured surface.

25. A method as claimed in claim 24, wherein the textured surface of the silicone rubber facilitates attachment of adherent cells.

26. A method as claimed in claim 24 or 25, wherein the textured surface of the silicone rubber provides an increased number of sites for attachment of cells relative to an untextured surface.

27. A method as claimed in claim 3, wherein pores of the silicone rubber provide sites of attachment for cells.

28. A method as claimed in claim 3, wherein the resultant mixture is shaped prior to curing.

29. A method as claimed in claim 3, wherein pores of the silicone rubber are 1 $\mu$m–0.5 mm in diameter.

30. A method as claimed in claim 3, wherein the porous silicone rubber is cut to a desired size or shape.

31. A method as claimed in claim 5 wherein the sacrificial filler is crystalline.

32. A method as claimed in claim 3 wherein the sacrificial filler is classified prior to contacting the silicone rubber precursor.

33. A method as claimed in claim 9, wherein the sacrificial filler is milled to a particle size of 0.05–1 $\mu$m.

34. A method as claimed in claim 9, wherein the sacrificial filler is milled to a particle size of 0.1–0.4 $\mu$m.

35. A method as claimed in claim 3, wherein the sacrificial filler is removed by dissolution in an aqueous solvent.

36. A method as claimed in claim 23, wherein the additive is glass, and serves to render the silicone rubber mechanically rigid.

37. A method as claimed in claim 28, wherein the resultant mixture is shaped prior to curing, by molding or extrusion.

38. A method as claimed in claim 29, wherein the pores are 10 $\mu$m–0.2 mm in diameter.

39. A method as claimed in claim 29, wherein the pores are 50 to 150 $\mu$m in diameter.

* * * * *